US012629209B2

(12) United States Patent
Lee et al.

(10) Patent No.: US 12,629,209 B2
(45) Date of Patent: May 19, 2026

(54) ARTIFICIAL INTELLIGENCE-BASED SYSTEMS AND METHODS FOR AUTOMATIC MEASUREMENTS FOR PRE-PROCEDURAL PLANNING

(71) Applicant: DasiSimulations LLC, Dublin, OH (US)

(72) Inventors: Beom Jun Lee, Atlanta, GA (US); Lakshmi Prasad Dasi, Dublin, OH (US)

(73) Assignee: DasiSimulations LLC, Dublin, OH (US)

( * ) Notice: Subject to any disclaimer, the term of this patent is extended or adjusted under 35 U.S.C. 154(b) by 172 days.

(21) Appl. No.: 18/193,765

(22) Filed: Mar. 31, 2023

(65) Prior Publication Data

US 2023/0310080 A1 Oct. 5, 2023

Related U.S. Application Data

(60) Provisional application No. 63/326,049, filed on Mar. 31, 2022.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *G06T 7/0012* (2013.01); *G06T 7/11* (2017.01);
(Continued)

(58) Field of Classification Search
CPC ... A61B 34/10; A61B 34/25; A61B 2034/105; A61B 2034/107; A61B 2034/256;
(Continued)

(56) References Cited

U.S. PATENT DOCUMENTS

| 8,009,887 B2 * | 8/2011 | Ionasec ................... G06T 17/20 |
| | | 382/128 |
| 8,771,189 B2 * | 7/2014 | Ionasec ................... G06T 7/262 |
| | | 600/443 |

(Continued)

FOREIGN PATENT DOCUMENTS

| CN | 110264465 A * | 9/2019 | .......... G06T 7/0012 |
| EP | 3588382 A1 | 1/2020 | |

OTHER PUBLICATIONS

Kruger, Nina et al. Cascaded neural network-based CT image processing for aortic root analysis [Online]. Jan. 23, 2022 [ Retrieved Jul. 9, 2025]. Retrieved from the Internet: <URL: https://pmc.ncbi.nlm.nih.gov/articles/PMC8873075/> (Year: 2022).*

(Continued)

*Primary Examiner* — King Y Poon
*Assistant Examiner* — Michelle Hau Ma
(74) *Attorney, Agent, or Firm* — Benesch Friedlander Coplan & Aronoff LLP

(57) ABSTRACT

A computer implemented method to automatically measure structural features of anatomies using an automatic measurement system, the method includes receiving medical images of the anatomies. The method includes detecting landmarks of the anatomies based on the medical images using an artificial intelligence (AI)-based model and constructing an anatomical structural model of the anatomies based on the detected landmarks. The method includes making quantifying measurements of selected structural features of the anatomical structural model and generating a report including the quantifying measurements.

25 Claims, 13 Drawing Sheets

100

102 Artificial intelligence-based landmarks detection

104 Landmark-guided aortic root segmentation

106 Automatic measurements

108 Generate and/or output a report of the measurement and/or recommendations

(51) Int. Cl.
  *G06T 7/00*      (2017.01)
  *G06T 7/11*      (2017.01)
  *G06T 7/73*      (2017.01)
  *G06T 17/00*     (2006.01)

(52) U.S. Cl.
  CPC .............. *G06T 7/73* (2017.01); *G06T 17/00*
        (2013.01); *A61B 2034/105* (2016.02); *G06T*
        *2200/04* (2013.01); *G06T 2200/24* (2013.01);
                *G06T 2207/20081* (2013.01); *G06T*
            *2207/20084* (2013.01); *G06T 2207/20092*
        (2013.01); *G06T 2207/20132* (2013.01); *G06T*
                            *2207/30048* (2013.01)

(58) Field of Classification Search
  CPC ... A61B 2034/102; G06T 7/0012; G06T 7/11;
            G06T 7/73; G06T 17/00; G06T 2200/04;
            G06T 2200/24; G06T 2207/20081; G06T
            2207/20084; G06T 2207/20092; G06T
            2207/20132; G06T 2207/30048; G06T
            7/0014; G06T 7/10; G06T 7/62; G06T
                    7/136; G06T 7/187; G16H 15/00
  See application file for complete search history.

(56)              References Cited

U.S. PATENT DOCUMENTS

| | | | | |
|---|---|---|---|---|
| 11,238,580 B2 * | 2/2022 | Laaksonen | ............. | G06V 10/25 |
| 2009/0279758 A1 | 11/2009 | Dikici et al. | | |
| 2020/0160527 A1 * | 5/2020 | Rapaka | ..................... | G06T 7/62 |
| 2020/0261157 A1 * | 8/2020 | Chen | ...................... | A61B 34/20 |
| 2021/0204856 A1 | 7/2021 | Dehghan Marvast et al. | | |

OTHER PUBLICATIONS

Noothout, Julia et al. Deep Learning-Based Regression and Classification for Automatic Landmark Localization in Medical Images [ Online]. Retrieved on Jul. 9, 2025]. Dec. 2020. Retrieved from the Internet: <URL: https://ieeexplore.ieee.org/document/9139480? source=IQplus > (Year: 2020).*
Tretter, Justin et al. Understanding the Aortic Root Using Computed Tomographic Assessment . . . [Online]. Nov. 8, 2021 [Retrieved on Jul. 10, 2025]. Retrieved from the Internet: <URL: https://www. ahajournals.org/doi/10.1161/CIRCIMAGING.121.013134> (Year: 2021).*
Queiros et al. Automatic 3D aortic annulus sizing by computed tomography in the planning of transcatheter aortic valve implantation [Online]. Dec. 30, 2016 [Retrieved on Dec. 1, 2025]. Retrieved from the Internet: <URL: https://www.sciencedirect.com/science/article/pii/S1934592516302908 > (Year: 2016).*
Elattar et al. Automatic aortic root landmark detection in CTA images for preprocedural planning of transcatheter aortic valve implantation [Online]. Oct. 23, 2015 [Retrieved on Dec. 1, 2025]. Retrieved from the Internet: <URL: https://pmc.ncbi.nlm.nih.gov/articles/PMC4751164/ > (Year: 2015).*
Kocka et al. Fully automated measurement of aortic root anatomy using Philips HeartNavigator computed tomography software: fast , accurate, or both? [Online]. Mar. 30, 2022 [Retrieved on Dec. 1, 2025]. Retrieved from the Internet: <URL: https://pmc.ncbi.nlm. nih.gov/articles/PMC8971741/ > (Year: 2022).*
Perry et al. A guide for pre-procedural imaging for transcatheter aortic valve replacement patients [Online]. Nov. 26, 2020 [ Retrieved on Dec. 1, 2025]. Retrieved from the Internet: <URL: https://pmc. ncbi.nlm.nih.gov/articles/PMC7690031/ > (Year: 2020).*
Ribeiro, H. B. et al., "Predictive Factors, Management, and Clinical Outcomes of Coronary Obstruction Following Transcatheter Aortic Valve Implantation", Journal of the American College of Cardiology, vol. 62, No. 17, 2013.
"Transcatheter Aortic Valve Replacemnt (Tavr)", May Clinic, 2020, http://www.mayoclinic.org/tests-procedures/transcatheter-aorticvalve-replacement/about//pac-20384698, last accessed Apr. 6, 2023.
Shad, R. et al., "Patient-Specific Computational Fluid Dynamics Reveal Localized Flow Patterns Predictive of Post-", Left Ventricular Assist Device Aortic Incompetence, Circulation: Heart Failure 14, No. 7(2021), https://DOI: 10.1161/CIRCHEARTFAILURE.120. 008034.
Hellmeier, F. et al., "Hemodynamic Modeling of Biological Aortic Valve Replacement Using Preoperative Data Only", Frontiers in Cardiovascular Medicine 7, (2021), https://doi:10.3389/fcvm.2020. 593709.
Reynolds, A. H., "Convolutional Neural Networks (CNNs)", (2019), https://anhreynolds.com/blogs/cnn.html, last accessed Apr. 6, 2023.
Nikhil, B. et al., "Fundamentals of Deep Learning; Designing Next-Generation Machine Intelligence Algorithms", 1 et.: O'Reilly Media, Inc. 2017.
Siddiqui, S. A., et al., "Automatic Fish Species Classification in Underwater Videos: Exploiting Pre-Trained Deep Neural Network Models to Compensate for Limited Labelled Data", ICES Journal of Marine Science (2018), 75(1), 374-389. https://doi:10.1093/icesjms/fsx109.
Hutson, M., "AI Researchers Allege That Machine Learning is Alchemy" (2018), Science, vol. 360 Issue 6388.
Ronneberger, O., et al., "U-Net: Convolutional Networks for Biomedical Image Segmentation", In: Navab, N., Hornegger, J., Wells, W., Frangi, A. (eds) Medical Image Computing and Computer-Assisted Intervention—MICCAI 2015. MICCAI 2015. Lecture Notes in Computer Science, vol. 9351. Springer, Cham. https://doi. org/10.1007/978-3-319-24574-4_28.
He., K., et al., "Deep Residual Learning for Image Recognition", 2016 IEEE Conference on Computer Vision and Pattern Recognition (CVPR) (2016). https://doi.org/10.1109/cvpr.2016.90.
Achenbach, S. et al., "SCCT expert consensus document on computed tomography imaging before transcatheter aortic valve implantation (TAVI)/transcatheter aortic valve replacement (TAVR)", Journal of Cardiovascular Computed Tomography (2012) 6, 366-380.
Ruder, S., "An Overview of Multi-Task Learning for Deep Learning", Library Catalog: ruder.io. (2017, https://www.ruder.io/multi-task/, last accessed Apr. 6, 2023.
Russakovsky, O., et al., "ImageNet Large Scale Visual Recognition Challenge", Paper presented at the IEEE Conference on Computer Vision and Pattern Recognition, 2009.
Zhong, Z., et al., "An Attention-Guided Deep Regression Model for Landmark Detection in Cephalograms", ArXiv Abs/1906.07549 (2019).
Astudillo, P., et al., "Automatic Detection of the Aortic Annular Plane and Coronary Ostia from Multidetector Computed Tomography", Journal of Interventional Cardiology, vol. 2020, Article ID 9843275, 9 pages, https://doi.org/10.1155/2020/9843275.
Zhang, J., et al., "Detecting Anatomical Landmarks From Limited Medical Imaging Data Using Two-Stage Task-Oriented Deep Neural Networks", IEEE Transactions on Image Processing, vol. 26, No. 10, Oct. 2017.
Noothout, J. M. H., et al., "Deep Learning-Based Regression and Classification for Automatic Landmark Localization in Medical Images", IEEE Transactions on Image Processing, vol. 39, No. 12, Dec. 2020.
Astudillo, P., et al., "Curriculum deep reinforcement learning with different exploration strategies: A feasibility study on cardiac landmark detection", Paper presented at the 13th International Joint Conference on Biomedical Engineering Systems and Technologies, (2020).
Jang, Y., et al., "Deep Reinforcement Learning with Explicit Spatio-Sequential Encoding Network for Coronary Ostia Identification in CT Images", Sensors 2021, 21, 6187.
O'Neil, A. Q., et al., "Attaining human-level performance with atlas location autocontext for anatomical landmark detection in 3D CT data", ECCV Workshops, (2018).
AI, W. A., et al., "Automatic aortic valve landmark localization in coronary CT angiography using colonial walk", PLoS One 13(7): e0200317, 2018.
Blanke, P., et al., "Computed tomography imaging in the context of transcatheter aortic valve implantation (TAVI) / transcatheter aortic valve replacement (TAVR): An expert consensus document of the

(56)        References Cited

OTHER PUBLICATIONS

Society of Cardiovascular Computed Tomography", JACC, Cardio Vascular Imaging 12, No. 1, 2019.

Pérez-García, F., et al., "Torchio: A Python Library for Efficient Loading, Preprocessing, Augmentation and Patch-Based Sampling of Medical Images in Deep Learning" Computer Methods and Programs in Biomedicine 208, (2021).

Ioffe, S., et al., "Batch Normalization: Accelerating Deep Network Training by Reducing Internal Covariate Shift", (2015).

Watkins, A.C., et al, "Valve Sizing," In Transcatheter Aortic Valve Replacement: A How-to Guide for Cardiologists and Cardiac Surgeons, 49-52: Springer International Publishing, 2018.

Immè, S., et al, "Transcatheter Aortic Valve Implantation: Medtronic Corevalve Evolut R." In Percutaneous Treatment of Left Side Cardiac Valves: A Practical Guide for the Interventional Cardiologist, 385-404: Springer International Publishing, 2018.

Nalluri, H. B., et al, "Anatomic Variability of Coronary Ostia in Adult Human Cadaveric Hearts." International Journal of Anatomy and Research 4, No. 1 (2016): 1905-11.

Forrestal, B.J., et al, "Risk of Coronary Obstruction and Feasibility of Coronary Access After Repeat Transcatheter Aortic Valve Replacement With the Self-Expanding Evolut Valve: A Computed Tomography Simulation Study". Circulation. Cardiovascular interventions, (2020).

Kitamura, M. et al, "Risk Assessment of Coronary Obstruction During Transcatheter Aortic Valve Replacement" JACC: Cardiovascular Interventions 15, No. 5 (2022): 496-507.

Lai, V., et al, "Towards a Science of Human-Ai Decision Making: A Survey of Empirical Studies", (2021).

International Search Report and Written Opinion issued in PCT Application No. PCT/US23/65189, mailing date Jun. 28, 2023.

Deng, J., et al., "ImageNet: A Large-Scale Hierarchical Image Database", paper presented at the IEEE Conference on Computer Vision and Pattern Recognition, 2009.

Extended European Search Report issued in European Patent Application No. 23782083.2 dated Dec. 17, 2025.

* cited by examiner

100

200

300

302                    304

Input CT Image    Centerpoint Detection Model    Cropped CT Image    Aortic Landmark Model    Predicted Landmarks

400

402

600

700

1000

Report Details

| Hospital: | Hospital | Receive Date: | 9/9/9999 |
|---|---|---|---|
| City/State: | City,State | Review Date: | 9/9/9999 |

Patient Information

| Name: | Name | BASI Patient ID: | P28 |
|---|---|---|---|
| Sex: | | STS: | |
| Age: | | Comments: | No comment |
| Native Valve: | Aortic | Native Valve Type: | Tricuspid |

Valve Sizing Details

| Make | Model | Size by Area | Size by Mean Diameter | Size by Perimeter (π x Diameter) |
|---|---|---|---|---|
| Edwards | SAPIEN | 26 mm | 26 mm | . |
| Medtronic | CoreValve, EVOLUT | . | 29 mm | 29 mm |

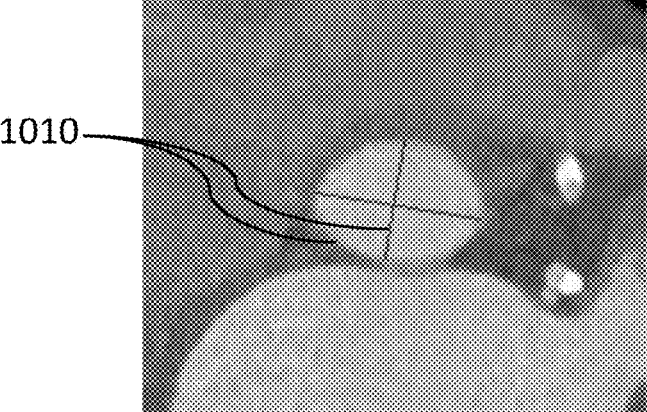

| Annulus Systole | |
|---|---|
| Area (mm²) | 448.23 |
| Perimeter (mm) | 76.16 |
| Diameter - Long (mm) | 27.1 |
| Diameter - Short (mm) | 21.5 |
| Area-derived diameter (mm) | 23.89 |
| perimeter-derived diameter (mm) | 24.24 |

1010

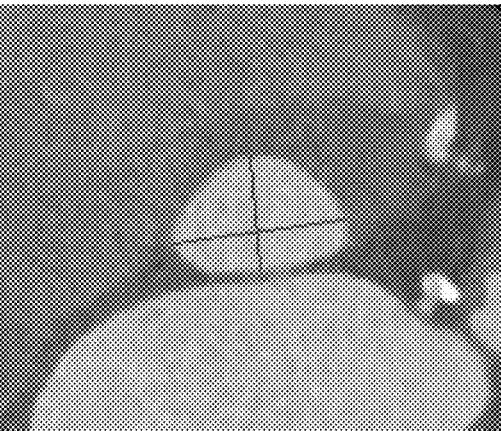

| Annulus Diastole | |
|---|---|
| Area (mm²) | 422.95 |
| Perimeter (mm) | 75.63 |
| Diameter - Long (mm) | 27.23 |
| Diameter - Short (mm) | 20.49 |
| Area-derived diameter (mm) | 23.21 |
| perimeter-derived diameter (mm) | 24.07 |

Cloud Database
1150

Automatic Measurement System 1100

Processing Unit 1110

System Memory 1120

Input Devices 1130

Output Devices 1140

ARTIFICIAL INTELLIGENCE-BASED SYSTEMS AND METHODS FOR AUTOMATIC MEASUREMENTS FOR PRE-PROCEDURAL PLANNING

PRIORITY

This application claims priority to U.S. Provisional Patent Application No. 63/326,049, filed Mar. 31, 2022, which is incorporated by reference herein in its entirety.

TECHNICAL FIELD

The present specification generally relates to systems and methods for automatic measurements for pre-procedural planning.

BACKGROUND

Structural analysis of patients' anatomies is essential for minimization of complications and the clinical success of many medical procedures and surgeries. Transcatheter Aortic Valve Replacement (TAVR) is one of such procedures that help treat aortic stenosis in a non-invasive manner through extensive pre-procedural planning via advanced medical imaging techniques. The pre-procedural evaluations for TAVR allow clinicians to determine the optimal valve type, size, and deployment strategies that would best prevent various adverse effects including elevated transvalvular pressure gradient, paravalvular leakage, aortic root rupture during implantation, coronary obstructions, etc. However, pre-TAVR evaluations typically involve an extensive, manual procedure of making measurements of multiple anatomic structures from cardiac computer tomography (CT) images which is both time-consuming and susceptible to inter-operator variability.

SUMMARY

A computer implemented method to automatically measure structural features of anatomies using an automatic measurement system, the method includes receiving medical images of the anatomies. The method includes detecting landmarks of the anatomies based on the medical images using an artificial intelligence (AI)-based model and constructing an anatomical structural model of the anatomies based on the detected landmarks. The method includes making quantifying measurements of selected structural features of the anatomical structural model and generating a report including the quantifying measurements.

A system for automatically measuring structural features of anatomies, the system includes a database and one or more automatic measurement systems connected to the database. Each of the one or more automatic measurement systems includes a non-transitory computer readable medium having stored thereon, a computer program having at least one code section for automatically measuring structural features of anatomies, the at least one code section being executed by at least a processor, causing an automatic measurement system to perform steps. The steps include receiving medical images of the anatomies and detecting landmarks of the anatomies based on the medical images using an artificial intelligence (AI)-based model. The steps include constructing an anatomical structural model of the anatomies based on the detected landmarks. The steps include making quantifying measurements of selected structural features of the anatomical structural model and generating a report including the quantifying measurements.

Other elements of the system and the method include the AI-based model including two independently trained convolutional neural networks.

Other elements of the system and the method include detecting the landmarks by inputting the medical images into a centerpoint detection model to generate cropped medical images and inputting the cropped medical images into an aortic landmark model to predict the landmarks of the anatomies.

Other elements of the system and the method include the steps that further include displaying visualization of the landmarks overlaid on the medical images.

Other elements of the system and the method include the steps that further include incorporating human input into the AI-based model and training the AI-based model based on the human input.

Other elements of the system and the method include incorporating human input by receiving inputs from a user to edit locations of the landmarks.

Other elements of the system and the method include incorporating human input by displaying the anatomical structural model and the quantifying measurements on a user-interactive dashboard and enabling a user to change an outline of the anatomical structural model or to re-measure the quantifying measurements using the user-interactive dashboard.

Other elements of the system and the method include the steps that include recording the human input and the quantifying measurements of a patient in the database and crosschecking and tracking the human input and the quantifying measurements about the patient recorded at different times.

Other elements of the system and the method include the system being configured to allow multiple users to access the database and retrieve intermediate and final results from the steps performed by the automatic measurement systems.

Other elements of the system and the method include the steps that further include generating the report comprising the quantifying measurements overlaid on the medical images.

Other elements of the system and the method include the steps that further include generating the report including recommendations of aortic valve sizing and type based on the quantifying measurements.

Other elements of the system and the method include that the selected structural features include annulus, Sinus of Valsalva, sinotubular junction (STJ), ascending aorta, left ventricular outflow junction (LVOT), aortic valve angulation, and/or coronary artery heights.

Other elements of the system and the method include the steps of receiving medical images including receiving computed tomography (CT) images, magnetic resonance imaging (MRI) images, ultrasonography, and/or positron emission tomography (PET) images.

BRIEF DESCRIPTION OF THE DRAWINGS

FIGS. 10A-10C each shows a part of an example report generated by the systems and methods disclosed herein, outlining the automatically generated measurements along with the sizing chart of two types of prosthetic valve based on manufacturer's recommendations in the Instructions for Use.

DETAILED DESCRIPTION

The present disclosure is directed to systems and methods to automatically generate measurements of aortic structures for pre-TAVR evaluation, leading to enhanced efficiency of the measurement process and the robustness of the anatomic measurements, and ultimately enhancing the effectiveness of the pre-procedural planning of TAVR.

Figure 1:
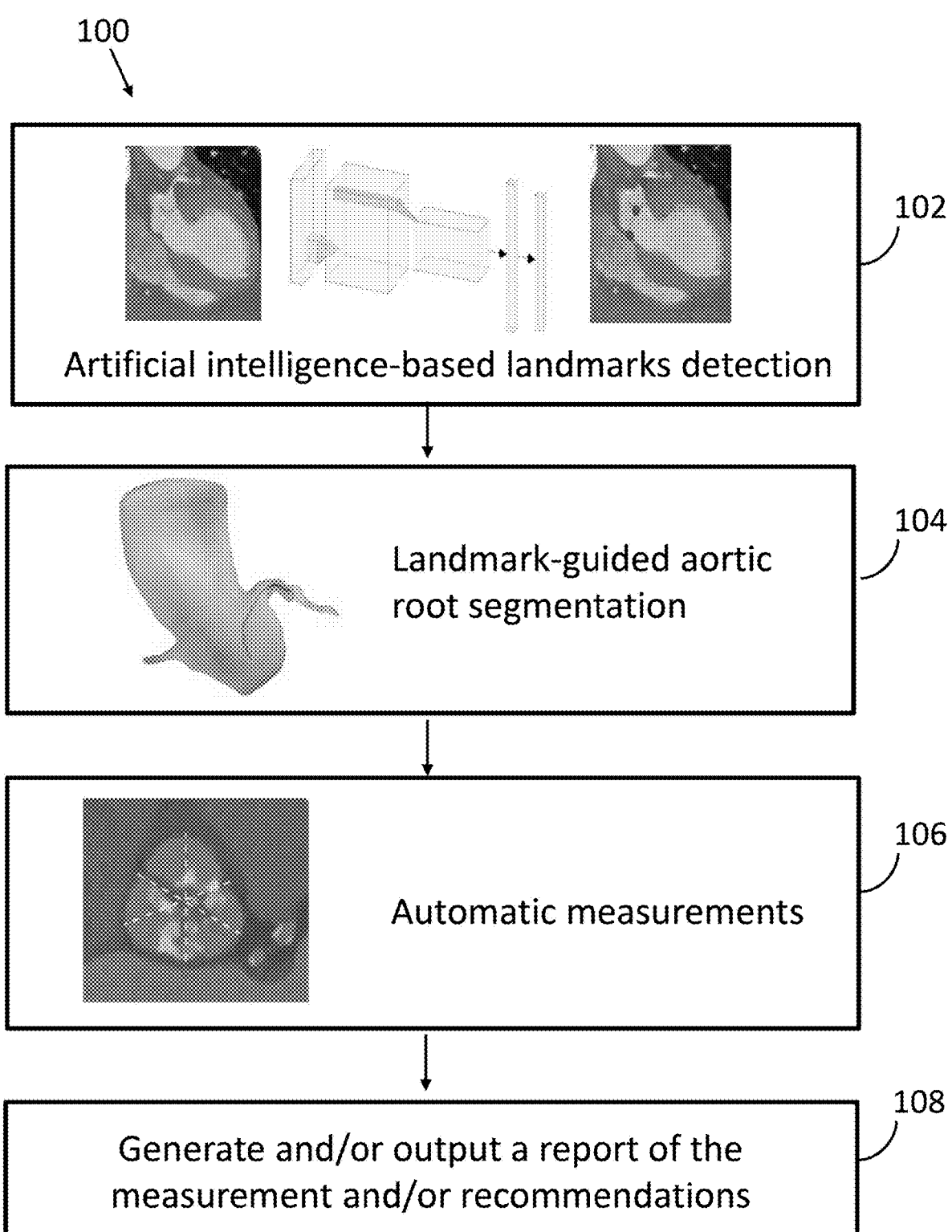
FIG. 1 is an example of a flow chart of an automatic segmentation and measurement of aortic anatomic features.

FIG. 1 shows an example flow chart of a method 100 disclosed herein for automatic reconstruction and measurement process. The method 100 includes three main steps: artificial intelligence-based landmarks detection (step 102), landmark-guided aortic root segmentation (step 104), and automatic measurements (step 106). In step 102, an artificial intelligence (AI)-based pipeline includes two convolutional neural networks used for the detection of a number of landmarks (e.g., 15 landmarks for example). In step 104, a landmark-guided segmentation of the aortic root is constructed. In step 106, measurements of essential aortic anatomies for pre-TAVR evaluation are performed automatically. In step 108, a report containing the measurement results and/or recommendations (for pre-procedural planning) is generated and/or outputted.

AI-Based Detection of Anatomical Landmarks

Figure 2:
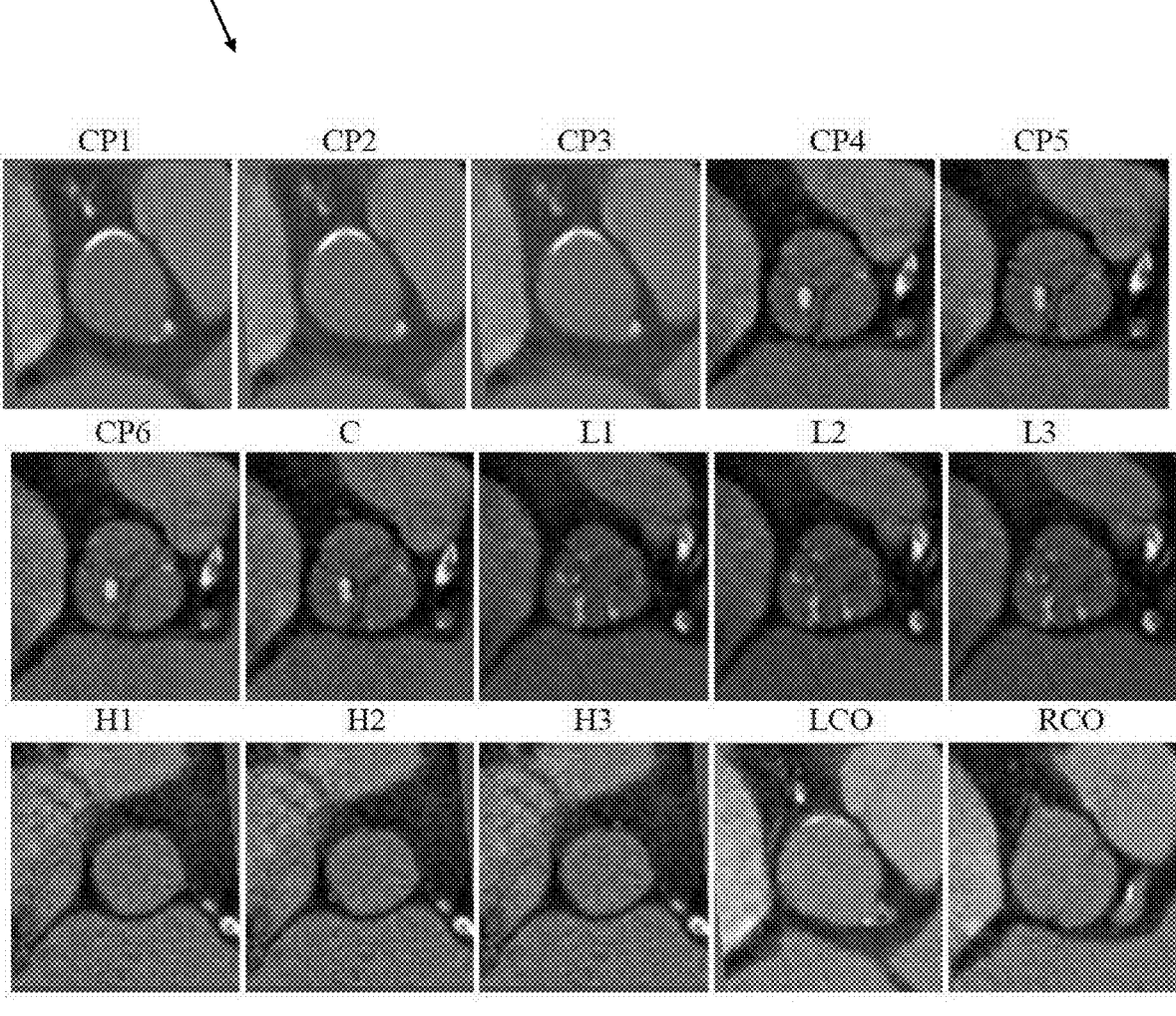
FIG. 2 is an example showing locations of fifteen landmark points that are detected and used for the segmentation of the aortic root structure.

In step 102, to initiate the automatic measurement process from imaging data (e.g., computed tomography or CT scan data, magnetic resonance imaging or MRI, ultrasonography, position emission tomography or PET, etc.), the image is inputted to an artificial intelligence (AI)-based pipeline that detects a number of distinct aortic landmarks. The total number of landmarks may be any suitable number. FIG. 2 shows a set of CT scan images 200 showing the locations of landmark points that are detected and used for the segmentation of the aortic root structure. In the illustrated example, there are 15 landmarks. CP1-3 and CP4-6 are six commissural points. These two sets of points are aimed at resolving the finite coaptation height between the leaflets at the commissure. For example, CP1 and CP4 are at the lower and upper ends of this finite commissural coaptation line. The landmark C is at the center coaptation point of the three leaflets. L1-3 are three surface points on the leaflets, while H1-3 are the three leaflet hinges. Finally, two points at the left and right coronary ostia (LCO and RCO) are detected for the segmentation of the coronary arteries.

Figure 3:
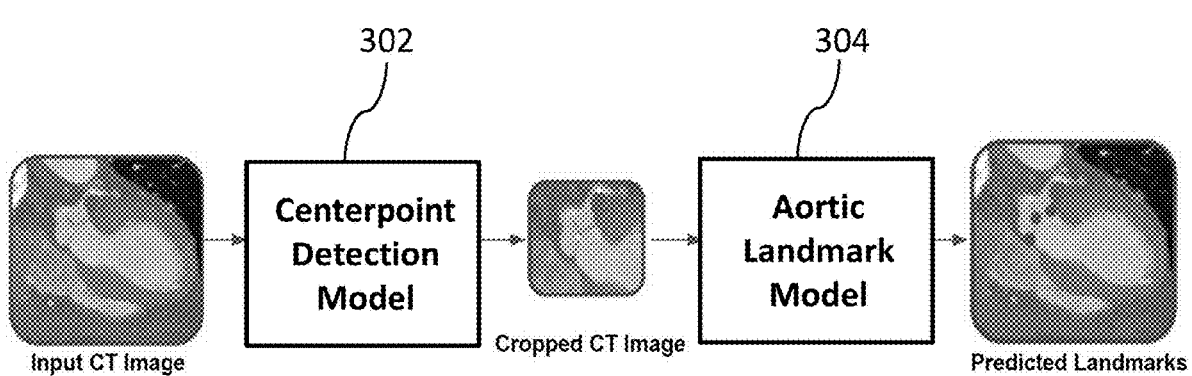
FIG. 3 is an example of a flow chart of an artificial intelligence (AI) model-based pipeline for the detection of the aortic landmarks from computer tomography (CT) images.

The AI-based pipeline consists of two independently trained convolutional neural networks as shown in a flow chart 300 in FIG. 3. The first of the two convolutional neural networks is a first model (the centerpoint detection model) 302 for the detection of the center of the aortic root. Trained with more than 100 pairs of cardiac CT images and manually created binary masks of the aortic root center, the centerpoint detection model 302 outputs a probability heatmap that signifies the probability of each of the voxels containing the aortic root based on the image features that the centerpoint detection model 302 captures from the training examples. The final predicted location of the aortic root center is determined by calculating the centroid of the heatmap. The predicted location of the aortic root center is used to crop the original CT image to a smaller volume, which is then fed into the second convolutional neural network for a finer detection of the fifteen aortic landmarks necessary to segment the aortic root anatomic features.

Working synergistically with the centerpoint detection model 302, the second convolutional neural network detects the fifteen aortic landmarks from images that are cropped around the center of the aortic root. Cropping of the image around the centerpoint allows for a finer detection of the aortic landmarks as a second model (the aortic landmark model) 304 gets to focus on a smaller region of the image that does not contain irrelevant information. The aortic landmark model 304 is trained and validated with the same cases as the centerpoint detection model 302. The ground-truth provided for algorithm/model training are manually labeled coordinates of the fifteen aortic landmarks. The aortic landmark model 304 detects image features from the training examples that help to discriminate the locations of the aortic landmarks from other irrelevant locations.

Figure 4:
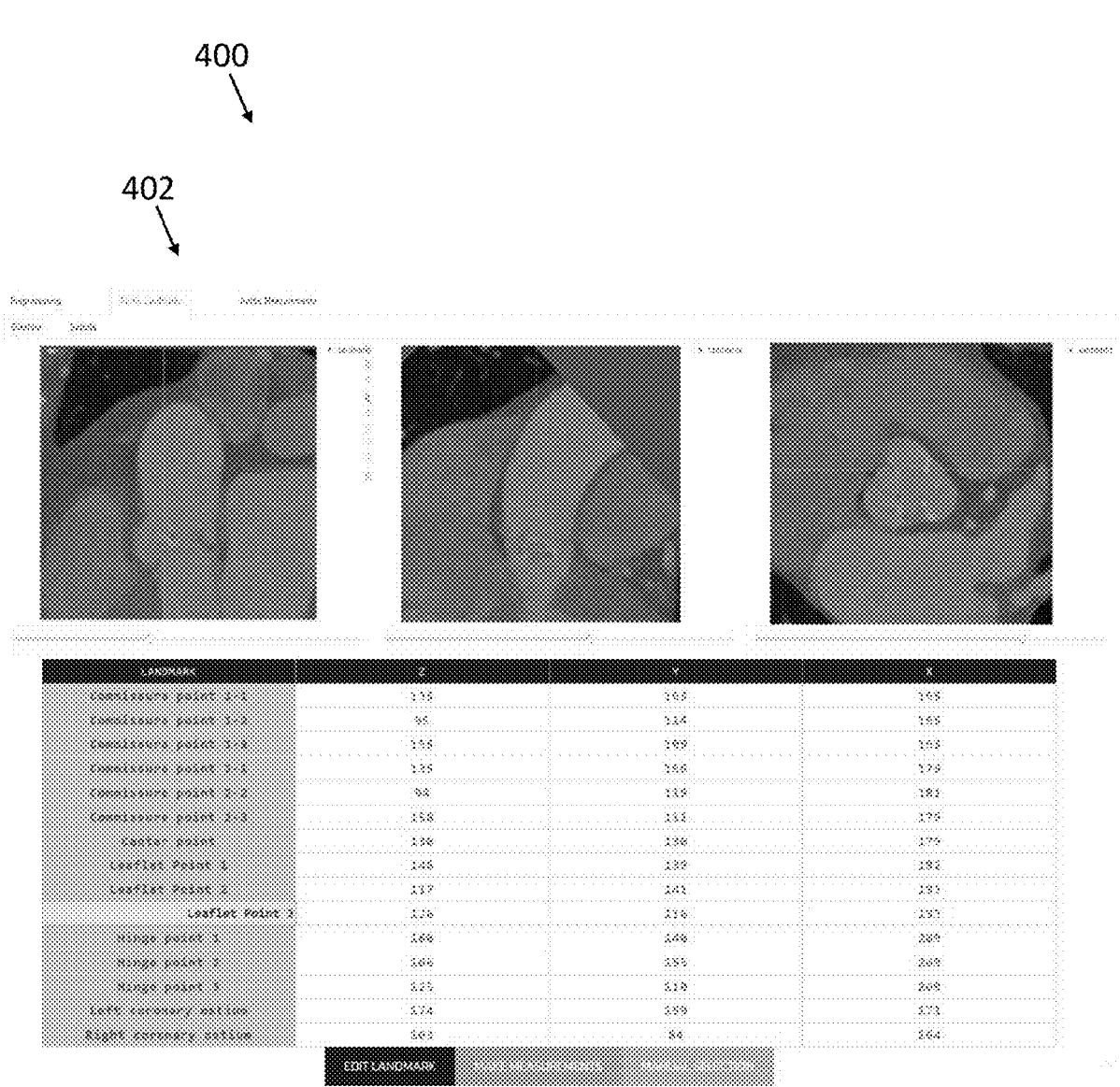
FIG. 4 is a snapshot of an example user-interactive dashboard's visualization of the AI-predicted aortic landmarks overlaid on the CT images.

Although the system can make the measurements from an input CT image without any manual inputs in a fully automatic manner, the intermediate and final outputs of the system such as the locations of predicted landmarks and the segmentation of the aortic root can be visualized and verified by a user through an interactive graphical user interface (GUI) dashboard. FIG. 4 displays an example of the visualization of the predicted landmarks through an interactive dashboard 400. A snapshot 402 of the user-interactive dashboard's visualization of the AI-predicted aortic landmarks overlaid on the CT images.

The user can visualize the landmarks to make sure that the predicted landmarks are accurate and also edit the locations of the landmarks manually (if needed). The manually refined landmarks can then be used for the training of the AI models, allowing for a streamlined, continuous improvement of the models' performance.

As shown in FIG. 4, the user can visualize the landmarks to make sure that the predicted landmarks are accurate and also edit the locations of the landmarks manually (if needed). The shown visualization interface allows the user to move the crosshairs to a desired location in order to move any of the aortic landmarks. The manually refined landmarks can then be used for the training of the AI models, allowing for a streamlined, continuous improvement of the models' performance as a human-in-the-loop system. Thus, the continual usage of the system will improve the accuracy of the AI-based models over time with further training.

Example 1

Example 1 describes an AI model architecture implemented to automatically detect anatomical landmarks in step 102. The architecture of the first convolutional neural network (the first model, the centerpoint detection model) features a variation on the U-Net, utilized in computer vision tasks. The architecture features a series of convolution layers followed by a series of transposed convolution (up-convolution) layers. Relevant image features needed to discriminate the centerpoint of the aortic root from other anatomical regions are learned from the convolution layers while the transposed convolutions utilize the image features to output a volumetric heatmap of each voxel's probability of containing the center of the aortic root. Such architecture is used for the initial coarse detection of the center of the aortic root as finer detection of important aortic landmarks including the centerpoint is performed in the second neural network (the second model, the aortic landmark model).

The architecture of the second AI model (the aortic landmark model) features a variation on the ResNet model for computer vision tasks. A ResNet model contains residual connections that prevent exploding gradients during training and thus allow for greater depth in the architecture's layers. Used in combination with a patch-based method, at the head of the architecture are two separate outputs: one vector for classification and another for regression. At the classification head, each input is classified as containing one or more landmarks of interest or not containing any. At the regression head, the displacements from each landmark to the center of the input are regressed.

During data processing, all input images are thresholded between a fixed range of intensity and resampled to the same resolution (1.5×1.5×1.5 mm/pixel for centerpoint model and 0.5×0.5×0.5×0.5×0.5×0.5×0.5 mm/pixel for aortic landmarks model). The images are of the same size, cropped around the detected centerpoint of the aortic root such that the cardiac anatomies around the aortic root are included within the images. As a part of the preprocessing step to optimize the training process, the intensities of the input images are normalized to be ranging between −1 and 1 and standardized to have 0 mean and unit standard deviation.

To train the centerpoint landmark (heatmap-based) model, the preprocessed input images in their original shape are input to the neural network. Mask volumes with spheres of a fixed radius at the aortic centers are provided for each image. The sizes of the mask volumes are the same as their corresponding input images. The network outputs a heatmap volume that signifies the probability of a given voxel containing the aortic landmark center. Finally, the center of mass of the heatmap is determined to be the centerpoint of the aortic root. The Euclidean distance between the predicted coordinates and the ground-truth coordinates is determined as the error of the model.

For training the aortic landmark (patch-based) model, the preprocessed input images are divided into 100×100×100 pixels patches and randomly fed into the neural network as the actual inputs. The coordinates of the manually labelled 15 aortic landmarks are provided. The neural network both classified the patches as either containing or not containing the landmarks of interest and regressed the vector from the center of the patch to the actual coordinates of the landmarks. During inference, a uniform sampling is executed such that patches of the same size are sampled uniformly across the input image volume. Like the centerpoint detection, the Euclidean distance between the predicted coordinates and the ground-truth coordinates of each of the 15 aortic landmarks are determined and averaged as the error.

For optimization of the centerpoint Landmark (heatmap-based) model, the Adam optimizer is used with a learning rate of 0.001. The model is trained for 100 epochs with early stopping. The loss function utilized is binary cross entropy using Equation 1, where $y_i$ and $\hat{y}_i$, represent the probability of a voxel containing the landmark of interest for the ground-truth and predicted volume, respectively:

$$L = -\sum_{i=1}^{N} y_i \log \hat{y}_i + (1 - y_i)\log(1 - \hat{y}_i) \qquad \text{Eq. 1}$$

For optimization of the aortic landmark (patch-based) model, the AdamW optimizer is used with an initial learning rate of 0.001. The model is trained for 250 epochs with early stopping. The loss function utilized is a combination of binary cross entropy and the absolute error loss (L1 loss) using Equation 2, where the variables with the subscript, c, represent the factors of the classification loss and those with the subscript r, represent the factors of the regression loss, and y and $\hat{y}$ are ground-truth and predicted landmark location, respectively:

$$L = -\left[\frac{1}{N}\sum_{i=1}^{N} y_{c,i} \log \hat{y}_{c,i} + (1 - y_{c,i})\log(1 - \hat{y}_{c,i})\right] + \left[\frac{1}{N}\sum_{i=1}^{N} |y - \hat{y}_{r,i}|\right] \qquad \text{Eq. 2}$$

Landmark-Guided Aortic Root Segmentation

Figure 5:
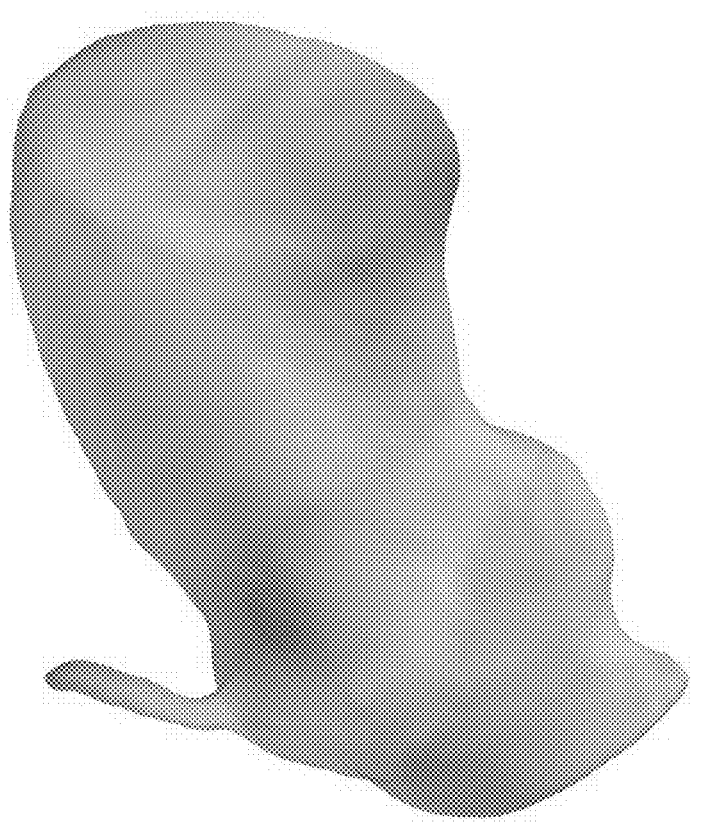
FIG. 5 is an example visualization of a 3D reconstruction of the aortic root generated by the landmark-guided segmentation algorithm.

In step 104, the landmark-guided automatic segmentation generates a 3D reconstruction of the aortic root from the CT images by utilizing the detected aortic landmarks as the structural information of the aortic root. The 3D reconstruction of the aortic root model may be achieved via systems and methods discussed in PCT/US2022/072240 filed May 11, 2022 and published as WO 2022/241425A1. In the present disclosure, the landmark-guided aortic root segmentation in step 104 may include an automatic segmentation algorithm utilizing a combination of adaptive thresholding method, image gradient-based method, and region-growing method to segment the aortic root wall and coronary arteries as individual sections. The segmented sections are then combined together to form a complete 3D reconstruction of the aortic root. FIG. 5 shows an example of a fully-assembled reconstruction of the aortic root generated by the segmentation algorithm in step 104.

Automatic Measurement of Aortic Structures

In step 106, measurements of aortic structures (e.g., the aortic structures generated in step 104) are performed automatically for pre-procedural planning. Given the 3D structure of the aortic root from the landmark-guided segmentation algorithm, the system disclosed inhere automatically makes accurate measurements of specific aortic structures including the annulus, Sinus of Valsalva, sinotubular junction (STJ), ascending aorta, left ventricular outflow junction (LVOT), aortic valve angulation, coronary artery heights, and/or other significant features.

Figure 6:
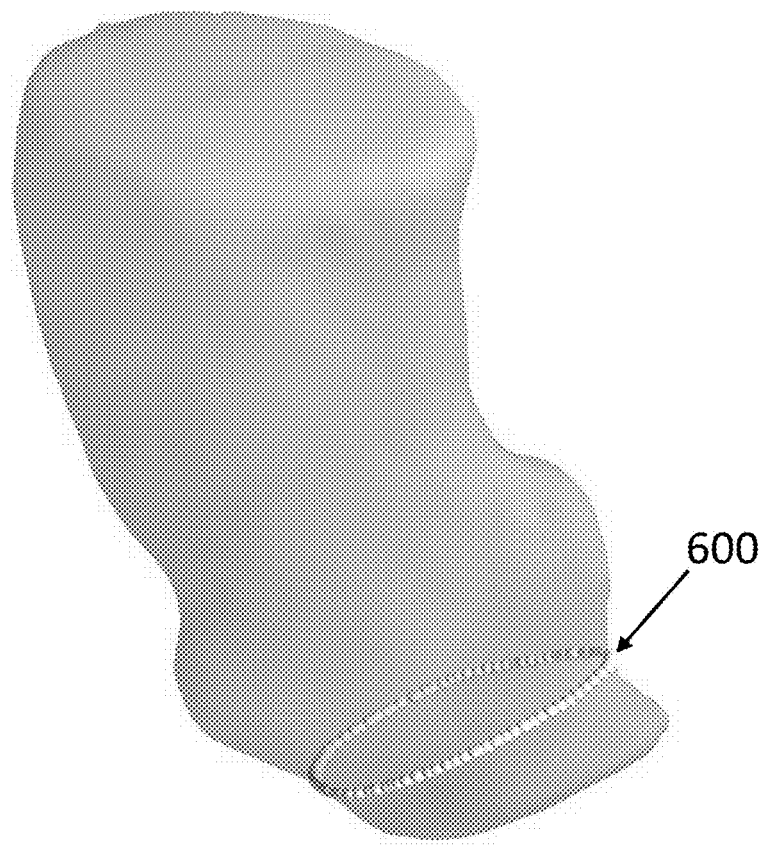
FIG. 6 is an example visualization of the annular plane overlaid on the 3D reconstruction of the aortic root.

Measurements are made by quantifying geometric features such as area, perimeter, and length (diameter and height) of the segmentation at specific locations along the aortic root. Locations of the measured aortic structures are inferred based on the detected aortic landmarks. For example, FIG. 6 shows a plane 600 at which the aortic annulus is measured, which is defined by the 3 hinge points (e.g., the three hinge points of the three aortic cusps that define the annular plane).

Figure 7:
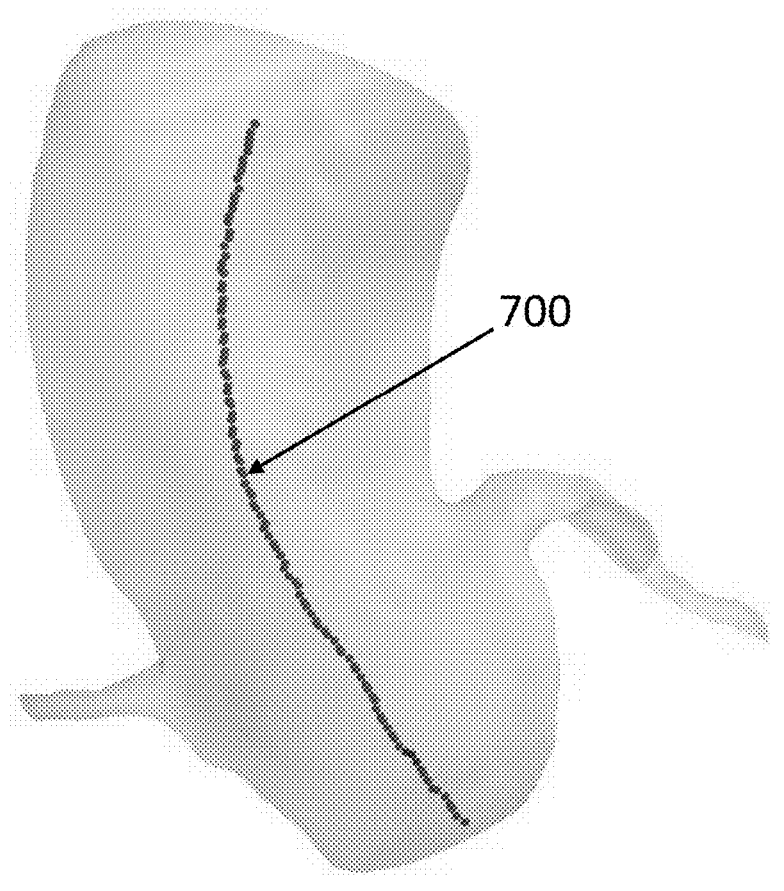
FIG. 7 is an example visualization of the detected centerline along the 3D reconstruction of the aortic root.

For example, FIG. 7 shows the detected centerline 700 along the aortic root. The centerline detection of the aortic root is based on the 3D reconstruction in order to determine the appropriate location of the STJ and ascending aorta, which are typically angled relative to the aortic annulus.

measurements and clinicians' measurements using the manufacturer's recommendations in the Instructions for Use. Table 1 displays how the recommended valve sizing based on automatic and clinical measurements shows good agreement as there is no oversizing/undersizing based on the automatic measurements as compared with the clinical manual measurements.

TABLE 1

| CT Dataset | Clinical Measurements | | | Automatic Measurements | | |
|---|---|---|---|---|---|---|
| | SAPIEN by area | EVOLUT by perimeter | EVOLUT by mean diameter | SAPIEN by area | EVOLUT by perimeter | EVOLUT by mean diameter |
| 1 | 29 | 34 | 34 2 | 29 | 34 | 34 |
| 2 | 23 | 26 | 26 | 23 | 26 | 26 |
| 3 | 26 | 29 | 29 | 26 | 29 | 29 |
| 4 | 26 | 29 | 29 | 26 | 29 | 29 |
| 5 | 26 | 29 | 29/34 | 26 | 29 | 29 |
| 6 | 26 | 29 | 29 | 26 | 29 | 29 |
| 7 | 26 | 29 | 29 | 26 | 29 | 29 |
| 8 | 23 | 26 | 26/29 | 23 | 26 | 26 |
| 9 | 23 | 26 | 26 | 23 | 26 | 26 |
| 10 | 23 | 26 | 26 | 23 | 26 | 26 |
| 11 | 20 | 23 | 23 | 20 | 23 | 23 |
| 12 | 26 | 29 | 29/34 | 26 | 29 | 29 |
| 13 | 23 | 26 | 26 | 23 | 26 | 26 |
| 14 | 29 | 29/34 | 34 | 29 | 29/34 | 34 |
| 15 | 26/29 | 29/34 | 34 | 29 | 29/34 | 34 |
| 16 | 23 | 26 | 26 | 23 | 26 | 26 |
| 17 | 20 | 26 | 26 | 20 | 26 | 26 |
| 18 | 26 | 29 | 34 | 29 | 29/34 | 34 |
| 19 | 26 | 29 | 29 | 26 | 29 | 29 |
| 20 | 26 | 29 | 29/34 | 26 | 29 | 29 |
| 21 | 23 | 26 | 26/29 | 23 | 26 | 26 |
| 22 | 26 | 29 | 29 | 26 | 29 | 29 |
| 23 | 20/23 | 26 | 26 | 23 | 26 | 26 |
| 24 | 23 | 26 | 26 | 23 | 26 | 26 |
| 25 | 26 | 29 | 29 | 26 | 29 | 29 |
| 26 | 26 | 29 | 29 | 26 | 29 | 29 |
| 27 | 26 | 29 | 29/34 | 26 | 29/34 | 34 |
| 28 | 26 | 29 | 29 | 26 | 29 | 29 |

Figure 8:
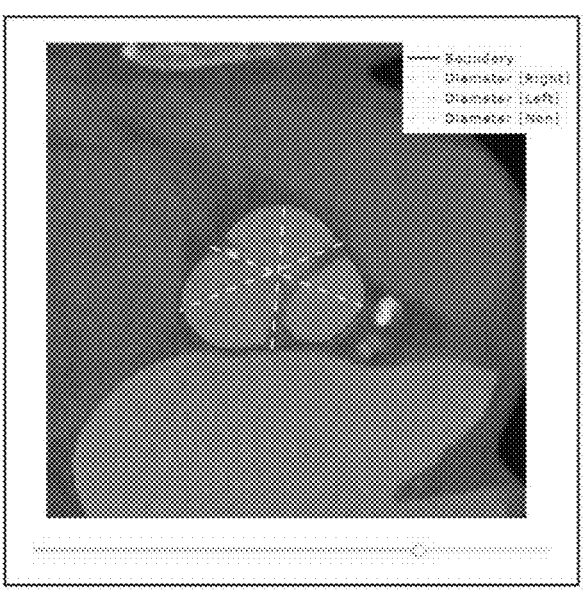
FIG. 8 is a snapshot of an example user-interactive dashboard's visualization of the segmentation and measurement of the aortic root.

Similar to the visualization of the AI-predicted landmarks, the segmentation and measurement of the aortic root are visualized through the user-interactive dashboard 400. Both the segmentation and measurements can be refined by the user by changing the outline of the segmentation or re-measuring any of the measurements via the GUI. FIG. 8 shows an example of the visualization of the segmentation and measurements of an aortic structure.

The system's measurement outputs can be gated with electrocardiogram (EKG) signals or respiration cycles for images containing multiple phases across heart beat or respiration. Thus, the user can obtain measurements pertaining to any particular phase in the cardiac cycle. Additionally, measurements can be tracked across the cardiac phases for temporal analysis.

A Comparison of Automatic Measurements with Clinical Measurements

Figure 9:
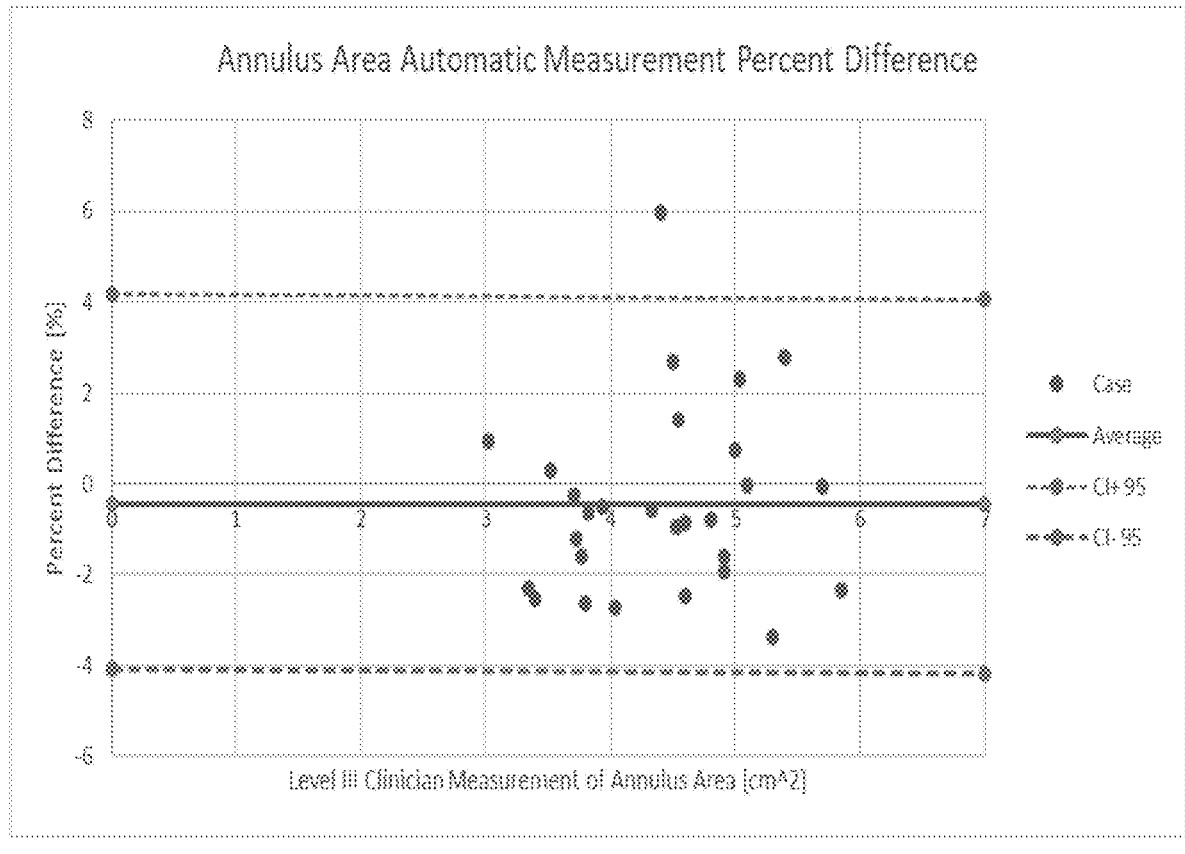
FIG. 9 shows a Bland-Altman plot of the automatic measurements of annulus area compared with clinician measurements across 28 individual cases.

To assess the accuracy of the automatic measurement process, a comparison with clinician measurements is shown in FIG. 9. In the illustrated example, 28 independent cases (from 28 different patients) are run through the automatic measurement process (as in FIG. 1), and their output annulus area measurements are compared with that of clinicians'. As shown by the Bland-Altman plot, the two groups show good agreement with an average percent error of −0.43%.

Two types of prosthetic valves, balloon-expandable and self-expanding valves, are sized based on both the automatic For example, based on clinical manual measurements done on the aortic root structure CT scan (dataset 1), a clinician may recommend a Sapien valve (manufactured by Edwards Lifesciences LLC) sizing 29 millimeters squared ($mm^2$) or an Evolut valve (manufactured by Medtronic) sizing 34 mm perimeter and 34 mm mean diameter. The automatic measurements approach disclosed herein show good agreement.

For example, based on clinical manual measurements done on the aortic root structure CT scan (dataset 2), a clinician may recommend a Sapien valve (manufactured by Edwards Lifesciences LLC) sizing 23 $mm^2$ or an Evolut valve (manufactured by Medtronic) sizing 26 mm perimeter and 26 mm mean diameter. The automatic measurements approach disclosed herein show good agreement.

It should be noted that the Sapien valve and Evolut valve are only given as examples, the automatic measurement system and method disclosed herein may make recommendations of heart valves from other manufacturers of suitable types and sizes.

Figure 10B:
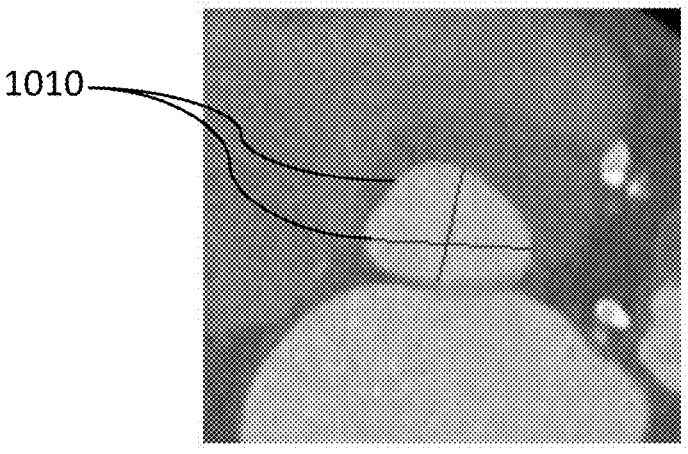
Figure 10B:
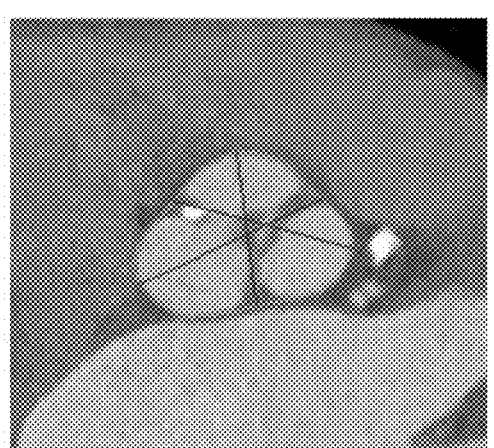
Figure 10B:
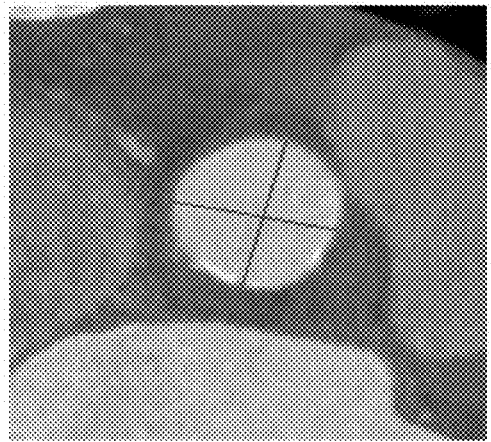
Figure 10B:
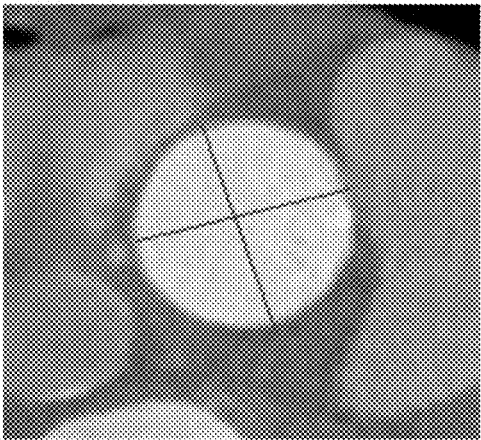
Figure 10C:
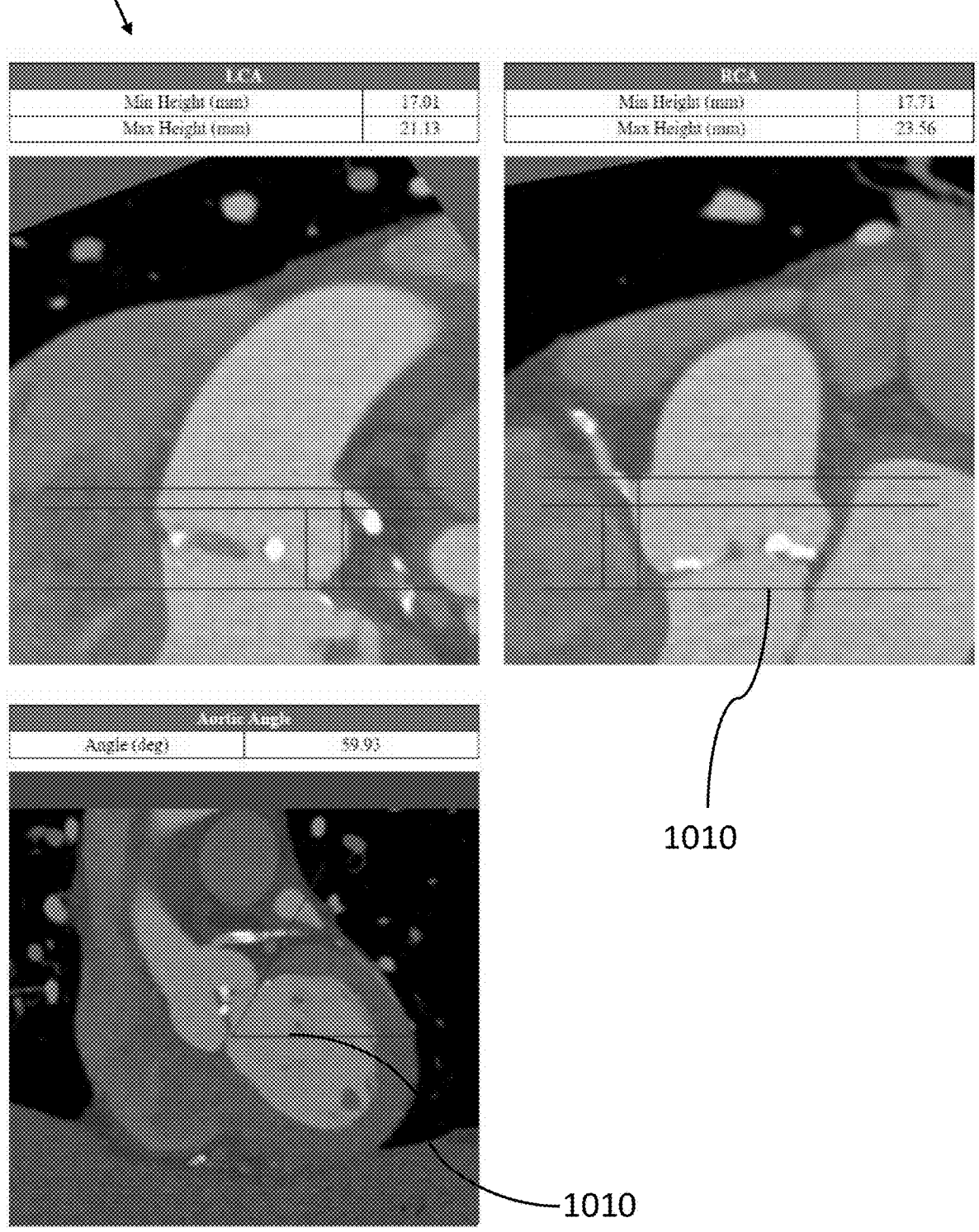

The automatic measurement system and method disclosed herein can also generate and output a report including measurements and recommendations (e.g., appropriate valve sizes for different types of prosthetic valves based on manufacturer guidelines). Specifically, the method 100 in FIG. 1 may include a step (step 108) for generating and/or outputting a report 1000 of the measurement and/or recommendations. The report 1000 may be in any suitable format. FIGS. 10A-10C show an example of the report 1000 generated by the automatic measurement system and method disclosed herein. The report 1000 may include measurements of the essential aortic anatomies (annulus, Sinus of Valsalva, sinotubular junction (STJ), ascending aorta, left ventricular outflow junction (LVOT), aortic valve angulation, and coronary artery heights, etc.) along with images that illustrate the automatic measurements overlaid on the original CT image and the recommended valve sizing of desired prosthetic valve type.

In FIG. 10A, the report 1000 includes patient information (e.g., name, sex, age, native valve, native valve type, etc.) and the recommended valve sizing details determined using the automatic measurement system and method disclosed herein. The valve sizing details include information of the valve make/manufacturer, model, and dimensions (e.g., size by area, size by mean diameter, size by perimeter, etc.).

In FIGS. 10A-10C, the report 1000 includes the measurements determined using the automatic measurement system and method disclosed. The measurements include the automatically measured sizing (e.g., area, perimeter, diameter long, diameter short, area-derived diameter, perimeter-derived diameter) of the annulus systole and annulus diastole, LVOT, Sinus, STJ, and Ascending Aorta. The measurements include the automatically measured sizing (e.g., minimum height and maximum height) of the left coronary artery (LCA) and right coronary artery (RCA) and the aortic angle. The automatic measurements marks 1010 are overlaid on the corresponding computed tomography or CT scan image.

Additionally, the report 1000 may include a copy of the Manufacturers Instructions for Use (IFU) of the recommended valve corresponding to the recommended valve sizing determined by the automatic measurement system and method disclosed herein. The IFU typically includes images and valve sizing chart(s) of the manufacturer.

The automatic measurement system can be utilized for multiple users. The system can record patient information and measurement results in a database, where it can cross-check and track any input information about the patient in order to provide individualized analyses. Accordingly, changes in anatomical measurements of any particular patient can be tracked for a long-term inspection or planning—an applicable feature for disciplines such as pediatrics or obstetrics and gynecology.

Similarly, the system can also be accessed by multiple users simultaneously. Users with independent login accounts can securely access intermediate and final outputs of relevant cases. For example, a clinician may refine the aortic landmarks or the measurement outputs of a particular case. Then, the edited landmark coordinates can be used for further AI-training upon verification.

Figure 11:
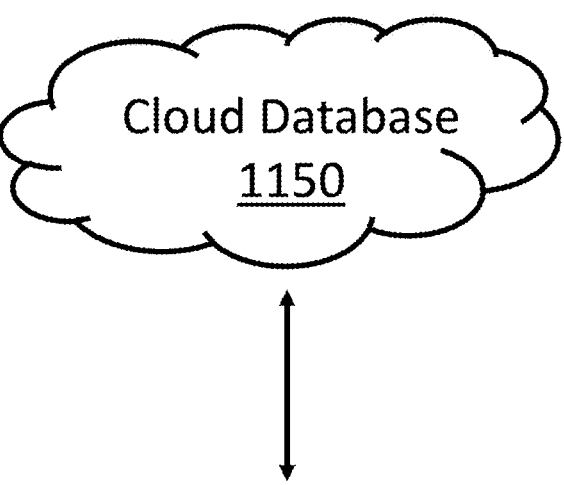
FIG. 11 shows an example of a system for automatic measurements of anatomical structures for pre-procedural planning.

FIG. 11 shows an illustrative computer architecture for an automatic measurement system 1100 capable of performing the automatic measurement method described herein. The computer architecture shown in FIG. 11 illustrates an example computer system configuration, and the automatic measurement system 1100 can be utilized to execute any aspects of the analysis and/or components presented herein or any components in communication therewith.

The automatic measurement system 1100 has computer environments appropriate (e.g., processor, memory, algorithms, controller, communication network, user interface, input device, output device, display, etc.) to receive and analyze data/information and determine and output results/recommendations.

In an aspect, the automatic measurement system 1100 may include one or more computers in communication with each other that collaborate to perform a task. In an aspect, the automatic measurement system 1100 may include a cloud computing environment. Cloud computing may comprise providing computing services via a network connection using dynamically scalable computing resources.

In its most basic configuration, the automatic measurement system 1100 typically includes at least one processing unit 1110 and system memory 1120 (e.g., non-transitory and/or transitory computer-readable medium).

The automatic measurement system 1100 includes input device(s) 1130 such as keyboards, keypads, switches, dials, mice, track balls, touch screens, voice recognizers, card readers, paper tape readers, or other well-known input devices.

The automatic measurement system 1100 includes output device(s) 1140 such as printers, video monitors, liquid crystal displays (LCDs), touch screen displays, displays, speakers, etc. may also be included. The additional devices may be connected to the bus in order to facilitate communication of data among the components of the automatic measurement system 1100. All these devices are well known in the art and need not be discussed at length here.

The various components may be in communication via wireless and/or hardwire or other desirable and available communication means, systems and hardware. The automatic measurement system 1100 may be connected to a cloud database 1150. More than one automatic measurement systems 1100 may be connected to the cloud database 1150 and data/information communicated and collected within the network can be used to enhance and refine the predication and measurements.

The automatic measurement system 1100 includes software and/or hardware components and modules needed to enable the function of the modeling, simulation, and methods disclosed in the present disclosure. In some aspects, the automatic measurement system 1100 includes artificial intelligence (A.I.) modules or algorithms and/or machine learning (M.L.) modules or algorithms (e.g., stored in the system memory 1120 and/or the cloud database 1150). The A.I. and/or M.L. modules/algorithms may improve the predictive power of the models, simulations, and/or methods disclosed in the present disclosure. For example, by using a deep learning, A.I., and/or M.L. model training including patient information and any relevant input data to the computational model, the predictive power of the computational model may be greatly enhanced. The A.I. and/or M.I. modules/algorithms also help improving sensitivity and specificity of the prediction as the database grows.

In some aspects, the automatic measurement system 1100 may include virtual reality (VR), augmented reality (AR) and/or mixed reality display(s), headset(s), glass(es), or any other suitable display device(s) as a part of the output device(s) 1140 and/or the input device(s) 1130. In some aspects, the display device(s) may be interactive to allow an user to select from options including with or without AR, with or without VR, or fused with real time clinical imaging to help clinician interact and make decisions.

In some aspects, the automatic measurement system 1100 may interface with a large language learning model to output a written or spoken description of the anatomical features and measurements. Accordingly, the outputs of the system can be automatically analyzed and summarized to provide detailed descriptions of the anatomical measurements and their implications for pre-procedural planning.

Although the types of the system's inputs are discussed in relation to computed tomography or CT scan images, the system can process multiple types of medical imaging including CT, magnetic resonance imaging (MRI), ultra-sonography, positron emission tomography (PET), echocardiography, etc.

Although an exemplary system and method is discussed in relation to aortic valve and TAVR, the exemplary system and method can be readily applied to the mitral valve and in other structural heart pre-procedural planning.

The exemplary system and method may be in daily clinical practices for TAVR and other structural heart pre-surgery evaluations.

The invention claimed is:

1. A computer implemented method for recommending a transcatheter aortic valve based on automatically measuring structural features of anatomies using an automatic measurement system, the method comprising:
   receiving medical images of the anatomies;
   detecting landmarks of the anatomies based on the medical images using an artificial intelligence (AI)-based model comprising two independently trained convolutional neural networks comprising a first AI model that is a centerpoint detection model for detection of a center of an aortic root and a second AI model that is an aortic landmark model based on a Res Net model;
   constructing an anatomical structural model of the anatomies comprising a left coronary artery (LCA) and right coronary artery (RCA) based on the detected landmarks;
   making quantifying measurements of selected structural features of the anatomical structural model, wherein the selected structural features comprise minimum and maximum heights of the LCA and the RCA and an aortic angle; and
   generating a report including the quantifying measurements and recommendations of sizing and type of the transcatheter aortic valve.

2. The computer implemented method of claim 1, wherein the detecting landmarks comprises:
   inputting the medical images into the centerpoint detection model to generate cropped medical images including the LCA and the RCA; and
   inputting the cropped medical images into the aortic landmark model to predict the landmarks of the anatomies.

3. The computer implemented method of claim 1, further comprising displaying visualization of the landmarks overlaid on the medical images.

4. The computer implemented method of claim 1, further comprising incorporating human input into the AI-based model and training the AI-based model based on the human input.

5. The computer implemented method of claim 4, wherein the incorporating human input comprises receiving inputs from a user to edit locations of the landmarks.

6. The computer implemented method of claim 4, wherein the incorporating human input comprises:
   displaying the anatomical structural model and the quantifying measurements on a user-interactive dashboard; and
   enabling a user to change an outline of the anatomical structural model or to re-measure the quantifying measurements using the user-interactive dashboard.

7. The computer implemented method of claim 4, further comprising:

recording the human input and the quantifying measurements in a database; and
   crosschecking and tracking the human input and the quantifying measurements recorded at different times.

8. The computer implemented method of claim 4, wherein the human input comprises annulus area measurements.

9. The computer implemented method of claim 1, further comprising generating the report comprising the quantifying measurements overlaid on the medical images.

10. The computer implemented method of claim 1, wherein the selected structural features further comprise annulus, Sinus of Valsalva, sinotubular junction (STJ), ascending aorta, left ventricular outflow junction (LVOT), and/or aortic valve angulation.

11. The computer implemented method of claim 1, wherein the receiving medical images comprises receiving computed tomography (CT) images, magnetic resonance imaging (MRI) images, ultrasonography images, and/or positron emission tomography (PET) images.

12. The computer implemented method of claim 1, wherein the landmarks comprise one or more of a first set of three commissural points, a second set of three commissural points, a finite coaptation height between leaflets at a commissure, three surface points on the leaflets, and three leaflet hinges.

13. A system for recommending a transcatheter aortic valve based on automatically measuring structural features of anatomies, comprising:
   a database;
   one or more automatic measurement systems connected to the database, wherein each of the one or more automatic measurement systems comprises:
      a non-transitory computer readable medium having stored thereon, a computer program having at least one code section for automatically measuring structural features of anatomies, the at least one code section being executed by at least a processor, causing an automatic measurement system to perform steps comprising:
      receiving medical images of the anatomies;
      detecting landmarks of the anatomies based on the medical images using an artificial intelligence (AI)-based model comprising two independently trained convolutional neural networks comprising a first AI model that is a centerpoint detection model for detection of a center of an aortic root and a second AI model that is an aortic landmark model based on a ResNet model;
      constructing an anatomical structural model of the anatomies comprising a left coronary artery (LCA) and right coronary artery (RCA) based on the detected landmarks;
      making quantifying measurements of selected structural features of the anatomical structural model, wherein the selected structural features comprise minimum and maximum heights of the LCA and the RCA and an aortic angle; and
   generating a report including the quantifying measurements and recommendations of sizing and type of the transcatheter aortic valve.

14. The system of claim 13, wherein the detecting landmarks comprises:
   inputting the medical images into the centerpoint detection model to generate cropped medical images including the LCA and the RCA; and inputting the cropped medical images into the aortic landmark model to predict the landmarks of the anatomies.

15. The system of claim 13, where the steps further comprise displaying visualization of the landmarks overlaid on the medical images.

16. The system of claim 13, wherein the steps further comprise incorporating human input into the AI-based model and training the AI-based model based on the human input.

17. The system of claim 16, wherein the incorporating human input comprises receiving inputs from a user to edit locations of the landmarks.

18. The system of claim 16, wherein the incorporating human input comprises:

displaying the anatomical structural model and the quantifying measurements on a user-interactive dashboard; and enabling a user to change an outline of the anatomical structural model or to re-measure the quantifying measurements using the user-interactive dashboard.

19. The system of claim 16, wherein the steps further comprise:

recording the human input and the quantifying measurements of a patient in the database; and crosschecking and tracking the human input and the quantifying measurements about the patient recorded at different times.

20. The system of claim 16, wherein the human input comprises annulus area measurements.

21. The system of claim 13 is configured to allow multiple users to access the database and retrieve intermediate and final results from the steps performed by the automatic measurement systems.

22. The system of claim 13, wherein the steps further comprise generating the report comprising the quantifying measurements overlaid on the medical images.

23. The system of claim 13, wherein the selected structural features further comprise annulus, Sinus of Valsalva, sinotubular junction (STJ), ascending aorta, left ventricular outflow junction (LVOT), and/or aortic valve angulation.

24. The system of claim 13, wherein the receiving medical images comprises receiving computed tomography (CT) images, magnetic resonance imaging (MRI) images, ultrasonography, and/or positron emission tomography (PET) images.

25. The system of claim 13, wherein the landmarks comprise one or more of a first set of three commissural points, a second set of three commissural points, a finite coaptation height between leaflets at a commissure, three surface points on the leaflets, and three leaflet hinges.

* * * * *